(12) United States Patent
Emarlou

(10) Patent No.: US 9,781,951 B2
(45) Date of Patent: Oct. 10, 2017

(54) MULTI-USER INHALATION ADATPOR

(71) Applicant: Hamid Emarlou, Los Gatos, CA (US)

(72) Inventor: Hamid Emarlou, Los Gatos, CA (US)

(*) Notice: Subject to any disclaimer, the term of this patent is extended or adjusted under 35 U.S.C. 154(b) by 838 days.

(21) Appl. No.: 14/254,723

(22) Filed: Apr. 16, 2014

(65) Prior Publication Data

US 2015/0296879 A1   Oct. 22, 2015

(51) Int. Cl.
*A24F 9/00* (2006.01)
*A24F 1/30* (2006.01)
*A24F 7/02* (2006.01)
*A61M 15/00* (2006.01)
*A61M 11/00* (2006.01)
*A61M 16/08* (2006.01)
*A24F 47/00* (2006.01)

(52) U.S. Cl.
CPC ............... *A24F 9/00* (2013.01); *A24F 1/30* (2013.01); *A24F 7/02* (2013.01); *A61M 11/00* (2013.01); *A61M 15/00* (2013.01); *A61M 16/0816* (2013.01); *A24F 47/008* (2013.01); *A61M 2205/84* (2013.01)

(58) Field of Classification Search
None
See application file for complete search history.

(56) References Cited

U.S. PATENT DOCUMENTS 3,889,690 A * 6/1975 Guarnieri .................. A24F 1/30
131/173
3,918,464 A * 11/1975 Kolodziej ................. A24F 1/30
131/173

* cited by examiner

*Primary Examiner* — Michael J Felton
(74) *Attorney, Agent, or Firm* — NetLawyers LLP; Benedict O'Mahoney

(57) ABSTRACT

The present invention is directed to a multi-user inhalation adapter comprising an apparatus which connects to a source of vapor device and allows several people to inhale vapor at the same time. Generally, the present invention will attach to a vaporizer. In another embodiment, the apparatus can attach to an adaptor that in turn attaches to a balloon storing vapor. The multi-user inhalation adaptor contains a vapor chamber which receives vapor from a vaporizer or other vapor source. Air channels regulated by valves route the vapor from the vapor chamber to nozzles for which the associated valves have been opened. The nozzles are connected to inhalation tubes, through which users can inhale the vapor.

12 Claims, 20 Drawing Sheets

MULTI-USER INHALATION ADATPOR

CROSS-REFERENCE TO RELATED APPLICATIONS

The present application claims the benefit of U.S. Provisional application Ser. No. 16/812,290, incorporated by reference herein and for which benefit of the priority date is hereby claimed.

FEDERALLY SPONSORED RESEARCH

Not applicable.

SEQUENCE LISTING OR PROGRAM

Not applicable.

FIELD OF INVENTION

The present invention generally relates to devices for the inhalation of volatile components of a substance, or more particularly to an apparatus for the vaporization of materials which can be utilized simultaneously by a plurality of users.

BACKGROUND OF THE INVENTION

Multi-user inhalation devices have been used for respiratory protective systems, such as may be used after an emergency situation has caused a noxious environment. These devices have sources of oxygen rich gas, valving systems to replenish breathable air, sensors, scrubbers and other means to filter out impurities. However, these devices tend to be large, expensive and inappropriate for use in the inhalation of vaporized substances. These systems would in many cases remove the vapors that the present invention delivers.

Multi-user inhalation devices for the ingestion of materials have been used for smoking substances. In some parts of the world, users smoke waterpipes as part of their culture and tradition. Social smoking may done with a single or double hose hookah, and sometimes even triple or quadruple hose hookahs are used. However, hookahs require a draw from the user to keep the smoked substance ignited and are used in a serial fashion. Additionally, such multi-user features are built into the design of the hookah itself, and cannot be readily transformed from a single user device to a multi-user device.

An invention is needed that specifically addresses the problem of providing a means for users of portable vaporizing devices to socially consume vaporized substances by providing an apparatus that is small, portable, and that can easily attach to a source of vaporized substance.

SUMMARY OF THE INVENTION

The multi-user inhalation adapter is an interface which connects to a source of vapor device and allows several people to vaporize at once. Generally, the present invention will attach to a vaporizer. In another embodiment, the apparatus can attach to an adaptor that in turn attaches to a balloon storing vapor. There are a plurality of nozzles on the multi-user inhalation adaptor, and in one embodiment, a central nozzle is always open to prevent overheating, and the remaining nozzles on the perimeter of the adapter have individual valves to open or close the airway to prevent vapor loss when not in use. They can be opened and closed depending on usage preference. Each nozzle on the multi-user inhalation adaptor can be connected to an individual inhalation tube.

The invention provides an enhanced social vaporizing experience, is portable, can easily convert a single user vaporizer to a multi-user vaporizer, can adapt to various sources of vapor, and provides a social and hygienic method to vaporize socially.

BRIEF DESCRIPTION OF THE DRAWINGS

A complete understanding of the present invention may be obtained by reference to the accompanying drawings, when considered in conjunction with the subsequent, detailed description, in which.

DETAILED DESCRIPTION

Before the invention is described in further detail, it is to be understood that the invention is not limited to the particular embodiments described, as such may, of course, vary. It is also to be understood that the terminology used herein is for the purpose of describing particular embodiments only, and not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed with the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein.

It must be noted that as used herein and in the appended claims, the singular forms "a", "an", and "the" include plural referents unless the context clearly dictates otherwise.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, if dates of publication are provided, they may be different from the actual publication dates and may need to be confirmed independently.

It should be further understood that the examples and embodiments pertaining to the systems and methods disclosed herein are not meant to limit the possible implementations of the present technology. Further, although the subject matter has been described in a language specific to structural features and/or methodological acts, it is to be understood that the subject matter defined in the appended claims is not necessarily limited to the specific features or acts described above. Rather, the specific features and acts described above are disclosed as example forms of implementing the claims.

Figure 1:
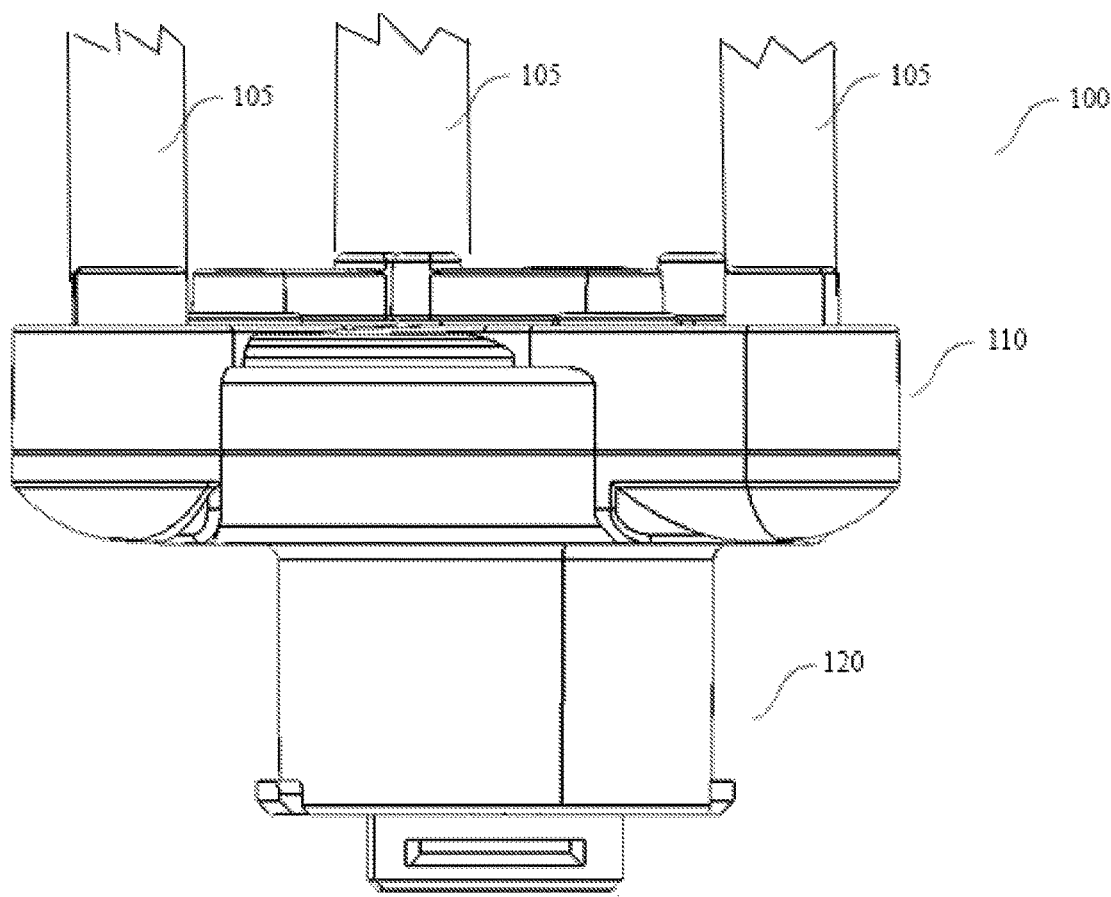
FIG. 1 is a side view diagram of a multi-user inhalation adaptor.

The present invention generally provides an apparatus allowing for multiple users to partake of vaporized substances using a vaporizer. In another embodiment of the present invention, a balloon adaptor is attached to the apparatus allowing for multiple users to partake of vaporized substances stored in a balloon. FIG. 1 shows a preferred embodiment of the present invention, a multi-user inhalation adaptor 100 comprising a plurality of inhalation tubes 105, which may be made of plastic tubing, along with an adaptor cap 110 and an adaptor base 120, which may be made of metal, plastic or other suitable material. In one embodiment, the adaptor cap 110 and adaptor base 120 are made of high heat and impact resistant nylon plastic fiber.

Figure 2:
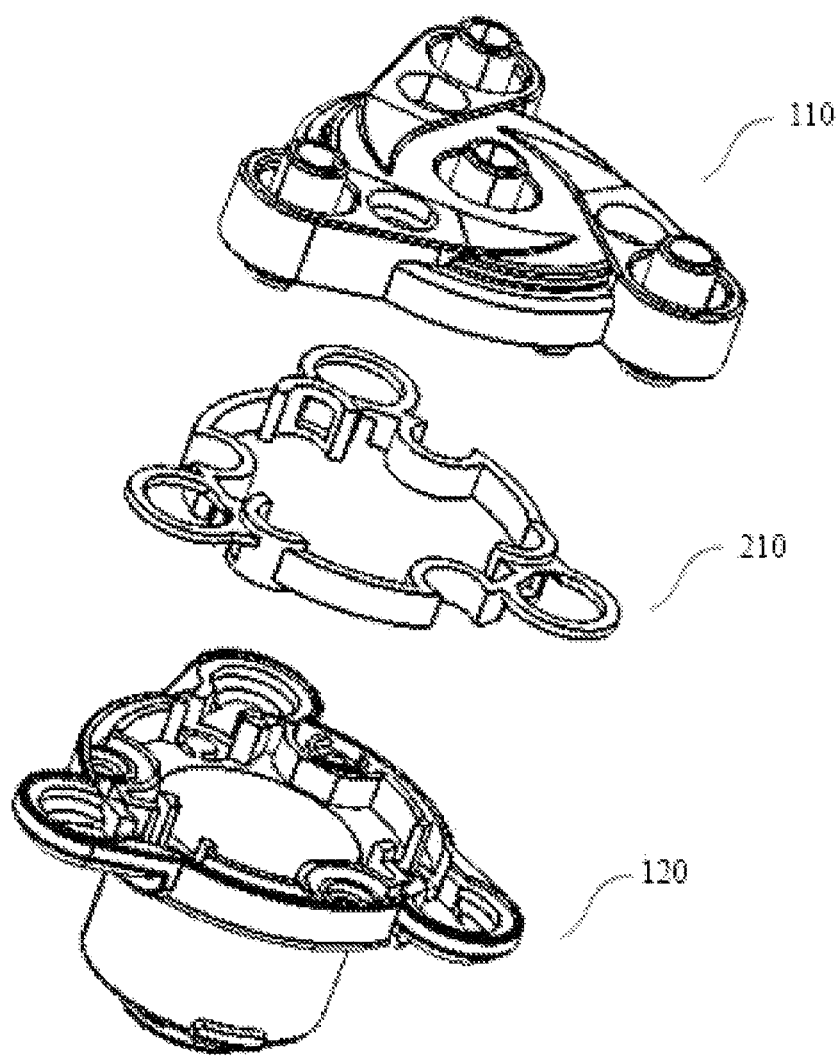
FIG. 2 is an oblique exploded view diagram of a multi-user inhalation adaptor.

In FIG. 2 is shown an exploded view of the multi-user inhalation adaptor 100 comprising an adaptor cap 110 configured to be fastened to an adaptor base 120 with a seal 210 configured to be positioned between the adaptor cap 110 and adaptor base 120. The seal 210 provides for creating airflow channels within the multi-user inhalation adaptor 100 in conjunction with described valves.

Figure 3:
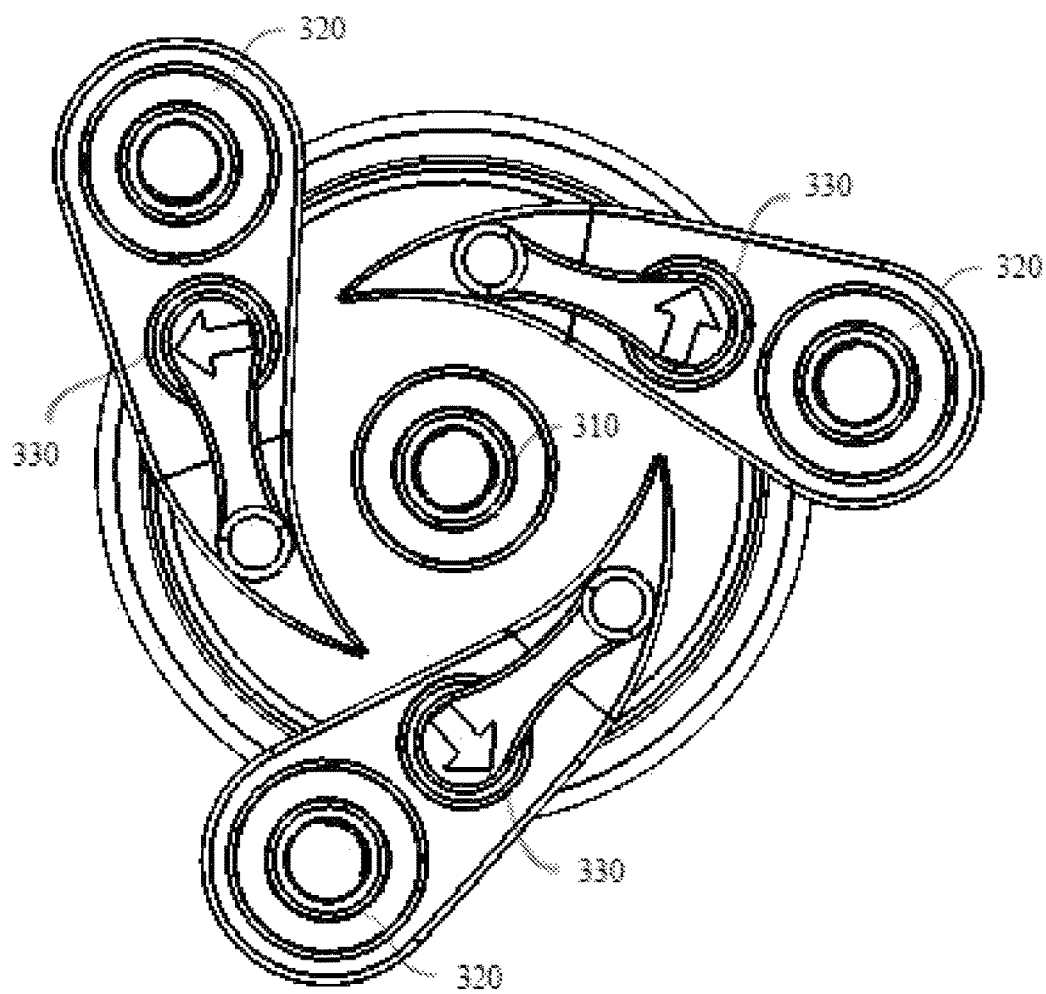
FIG. 3 is a top view diagram of a multi-user inhalation adaptor.

Turning now to FIG. 3, shown is a top view of the multi-user inhalation adaptor 100 showing the exterior top of the adaptor cap 110 in which can be seen a central nozzle 310 located in the center of the adaptor cap 110 and three perimeter nozzles 320 located on the perimeter of the adaptor cap 110. Additionally, adjacent to each perimeter nozzle 320 is perimeter nozzle valve 330 configured to constrict or expand airflow from the interior of the multi-user inhalation adaptor 100 to the perimeter nozzle 320. When a perimeter nozzle valve 330 is rotated to a particular position, the valve flange in conjunction with the seal 210 and the molding on the bottom interior of the adaptor cap 110 and the top interior of the adaptor base 120 create an air channel from a vapor chamber on the interior of the multi-user inhalation adaptor 100 to the perimeter nozzles 320. Each perimeter nozzle is configured to accept tubing from which users can readily inhale vapors utilizing the apparatus. There is no valve associated with the central nozzle 310, which always remains open. This serves the function of the device which can be used as a single user device when all of the perimeter nozzle valves 330 are set to the closed position, and prevents the device from overheating. Each of the perimeter nozzle valves 330 control the airflow to an associated perimeter nozzle 320, allowing for a variable number of users. Each perimeter nozzle 320 can be connected to an individual inhalation tube.

Figure 4:
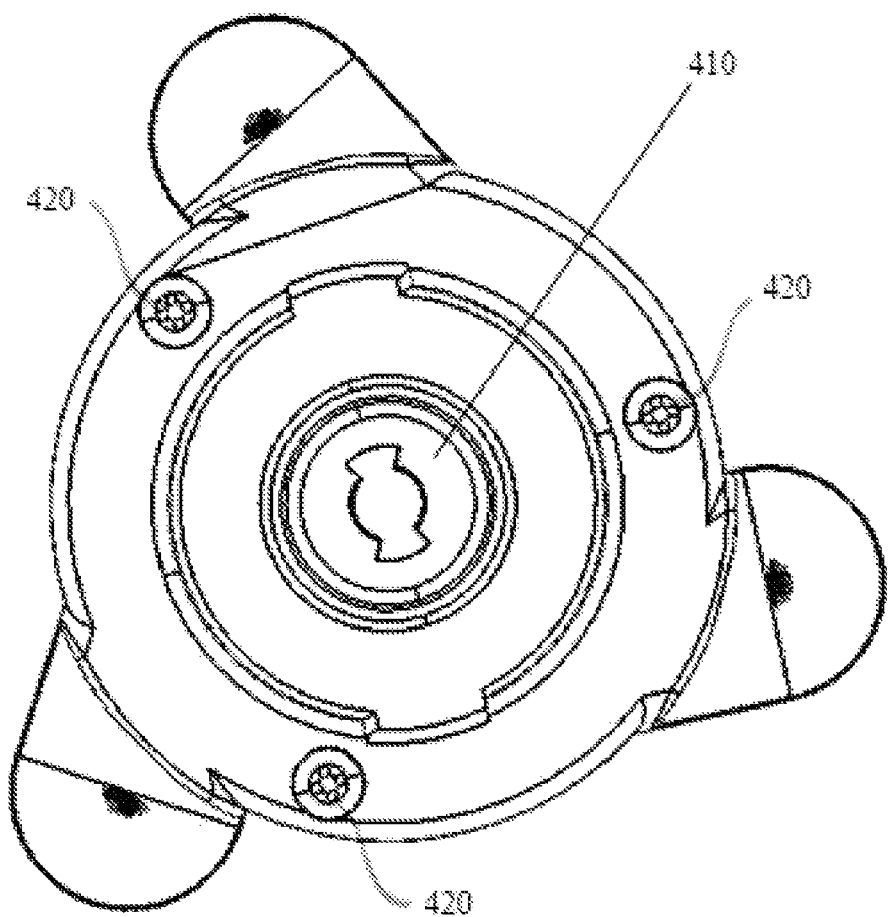
FIG. 4 is a bottom view diagram of a multi-user inhalation adaptor.

Turning now to FIG. 4, shown is a bottom view diagram of a multi-user inhalation adaptor 100 showing the exterior bottom of the adaptor base 120 with a vapor chamber intake vent 410 located in the center. Additionally shown are three screw holes 420 configured to allow insertion of a screw through the hole to fasten the adaptor base 120 to the adaptor cap 110. The vapor chamber intake vent 410 is the portion that interfaces with the vapor source, and through which the vapor flows through to the vapor chamber.

Figure 5:
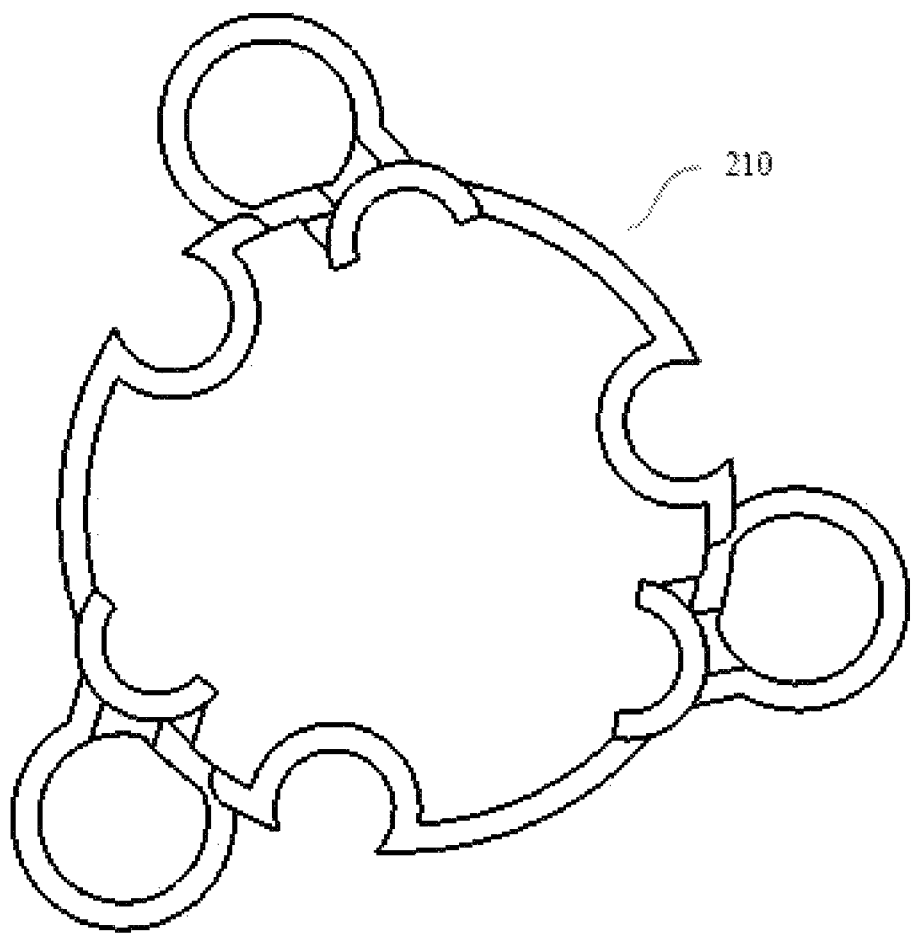
FIG. 5 is a bottom view diagram of a seal.

Turning now to FIG. 5, shown is a bottom view diagram of the seal 210 configured to be positioned between the bottom interior of the adaptor cap 110 and the top interior of the adaptor base 120, and which provides a means to control airflow between the vapor chamber through the perimeter nozzle valves 330 to the perimeter nozzles 320. The seal 210 is made of a pliable material such that it forms a gasket between the interior of the adaptor cap 110 and the top interior of the adaptor base 120.

Figure 6:
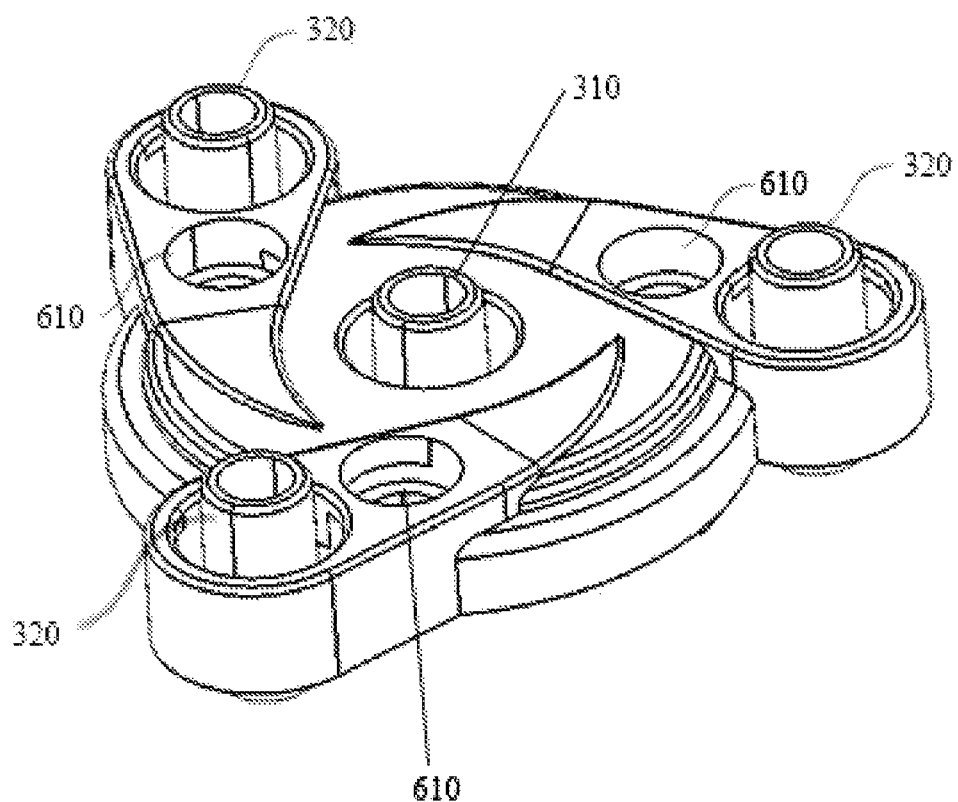
FIG. 6 is a top oblique view diagram of an adaptor cap.
Figure 7:
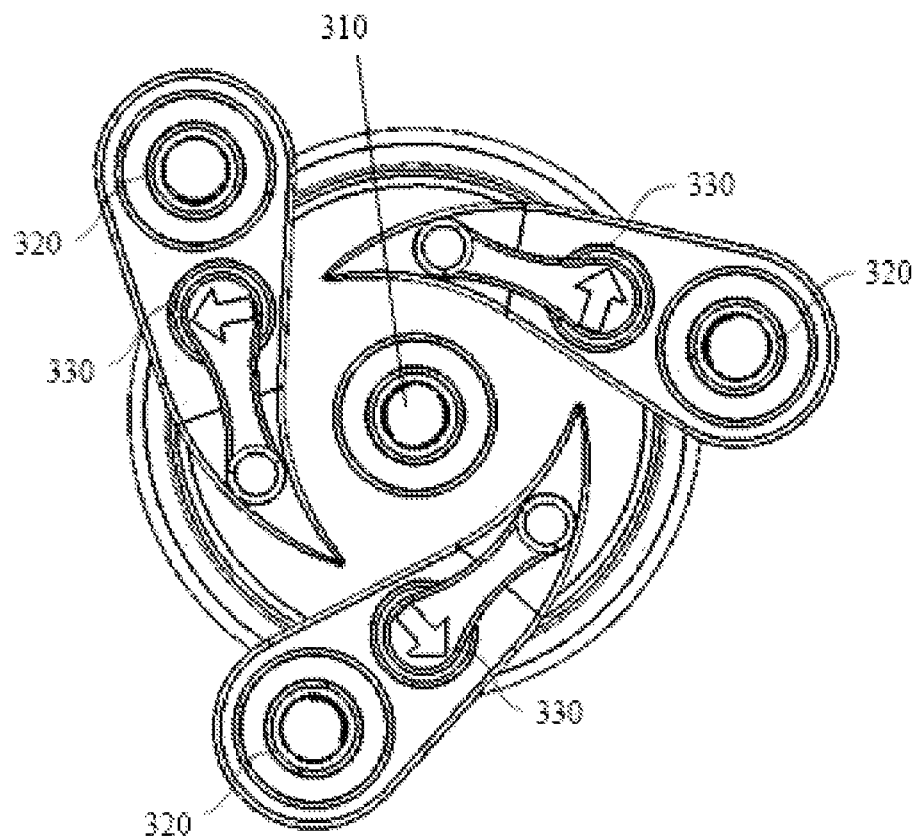
FIG. 7 is a top view diagram of an adaptor cap.

Turing now to FIG. 6, shown is a top oblique view diagram of the adaptor cap 100 showing the central nozzle 310, the three perimeter nozzles 320 and three valve orifices 610, each configured to accept seating of a perimeter nozzle valve 330. When seated in a valve orifice 610, a perimeter nozzle valve 330 can be rotated to an open position to allow vapor to pass through from a vapor chamber to an associated perimeter nozzle 320. FIG. 7 is a top view diagram of the adaptor cap 110 showing the central nozzle 310, the three perimeter nozzles 320 and the three perimeter nozzle valves 330.

Figure 8:
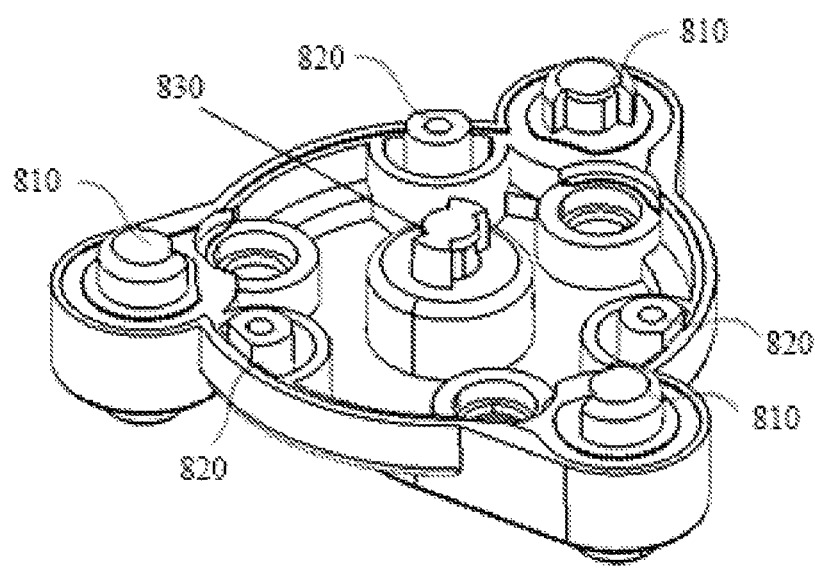
FIG. 8 is a bottom oblique view diagram of an adaptor cap.
Figure 9:
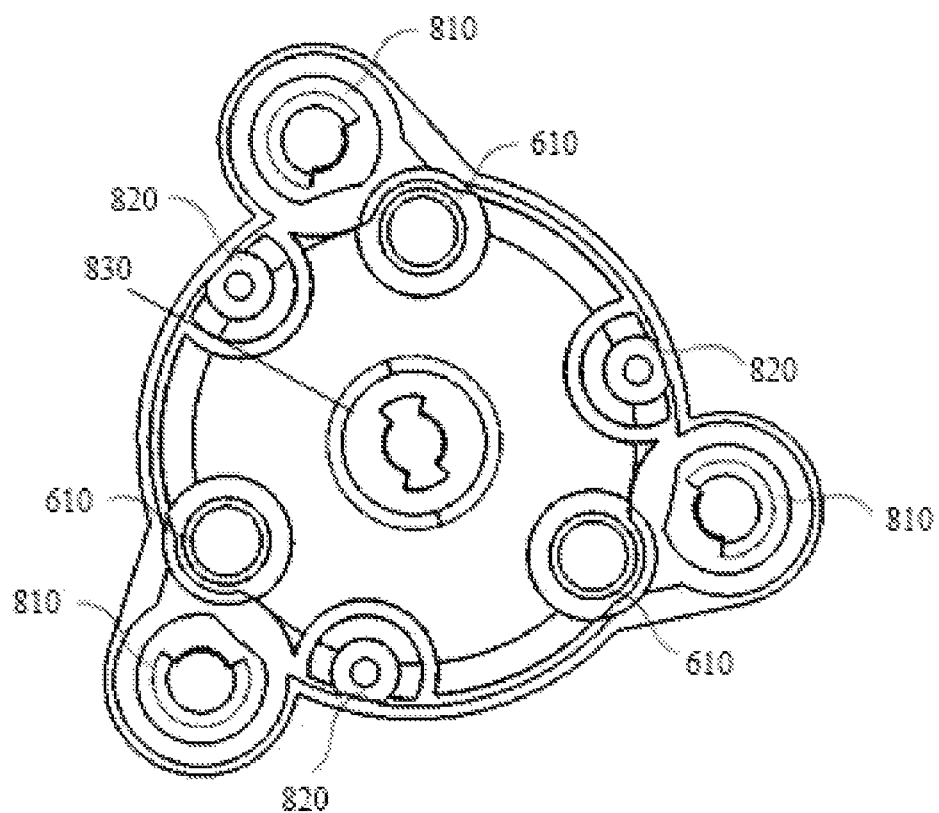
FIG. 9 is a bottom view diagram of an adaptor cap.

Turning now to FIG. 8, shown is a bottom oblique view diagram showing the bottom interior of the adaptor cap 110. The diagram shows three perimeter nozzle intake valves 810, three screw anchors 820, and a central nozzle intake vent 830. FIG. 9 is a bottom view diagram showing the bottom interior of the adaptor cap 110. The diagram shows the three valve orifices, the three perimeter nozzle intake vents 810, the three screw anchors 820, and the central nozzle intake vent 830.

Figure 10:
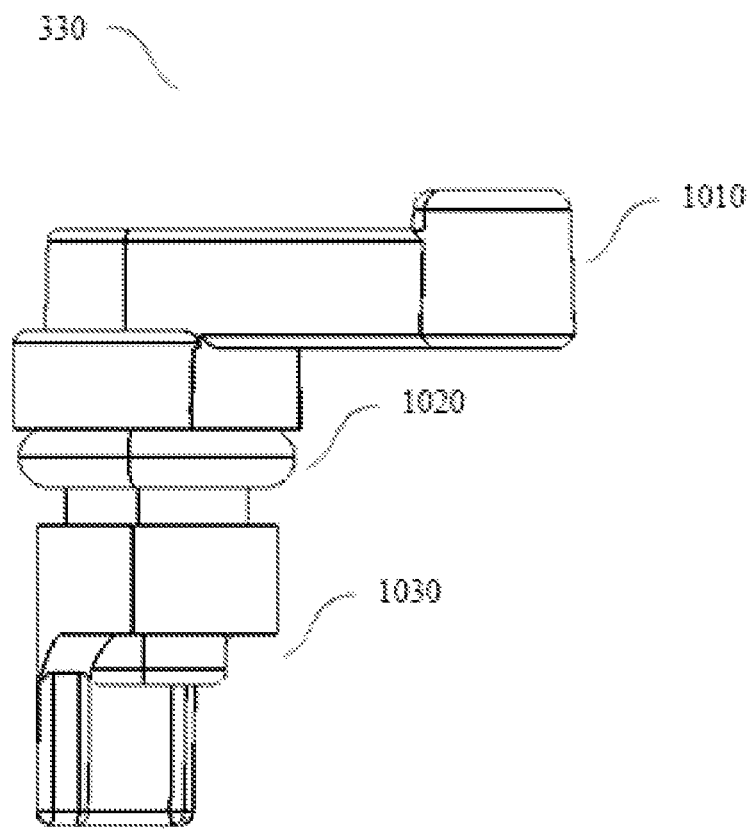
FIG. 10 is a side view diagram of a valve.

Turning now to FIG. 10, shown is a side view diagram of the valve 330 comprising a valve handle 1010, a valve O-ring 1020, and a valve flange 1030 in which the valve handle 1010 is fixedly connected to the valve flange 1030 and the valve O-ring 1020 circumscribes the upper portion of the valve flange 1030. When positioned in a valve seat, the perimeter nozzle valve regulates the flow of vapor from the vapor chamber to the associated perimeter nozzle.

Figure 11:
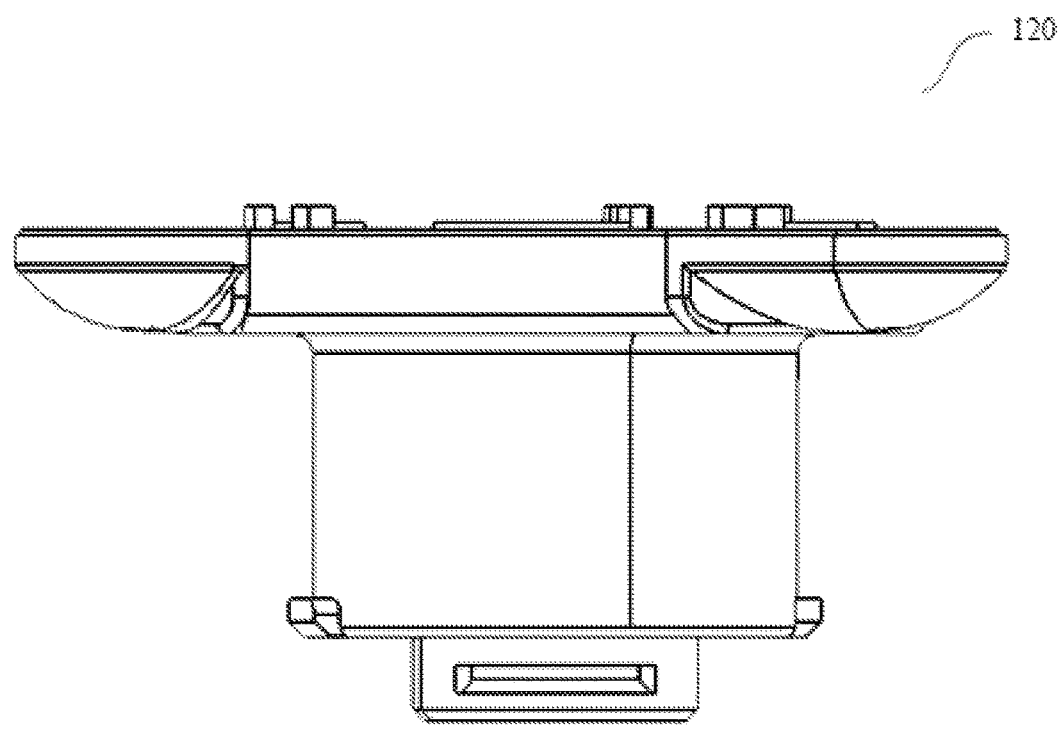
FIG. 11 is a side view diagram of an adaptor base.
Figure 12:
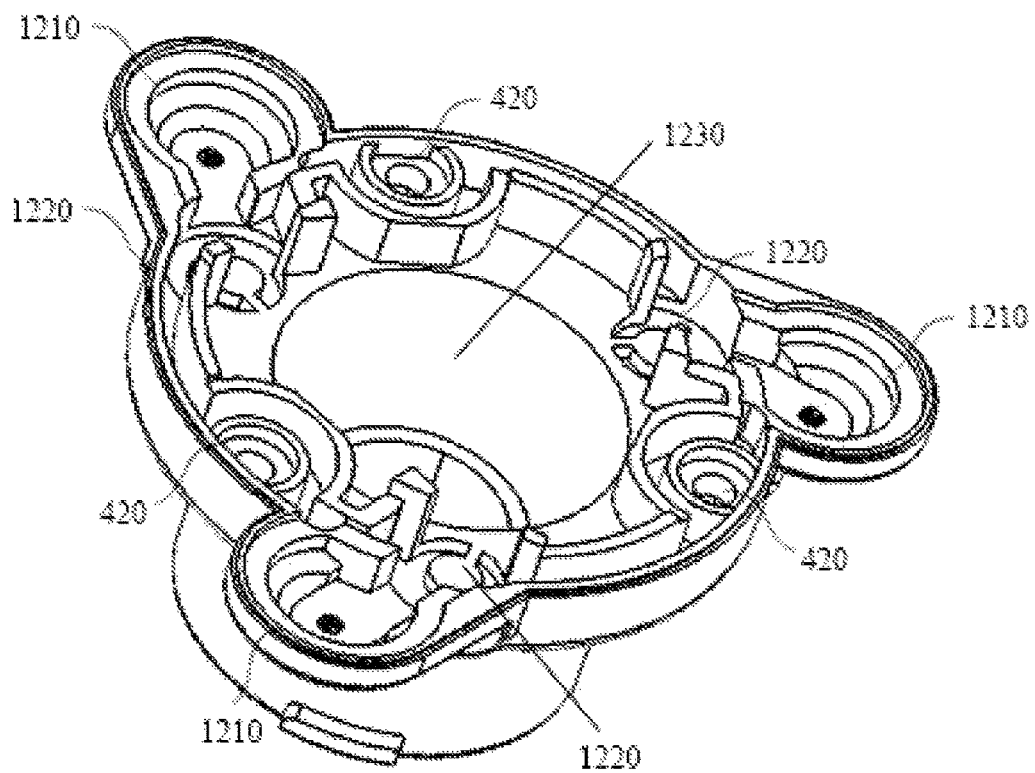
FIG. 12 top oblique view diagram of an adaptor base.
Figure 13:
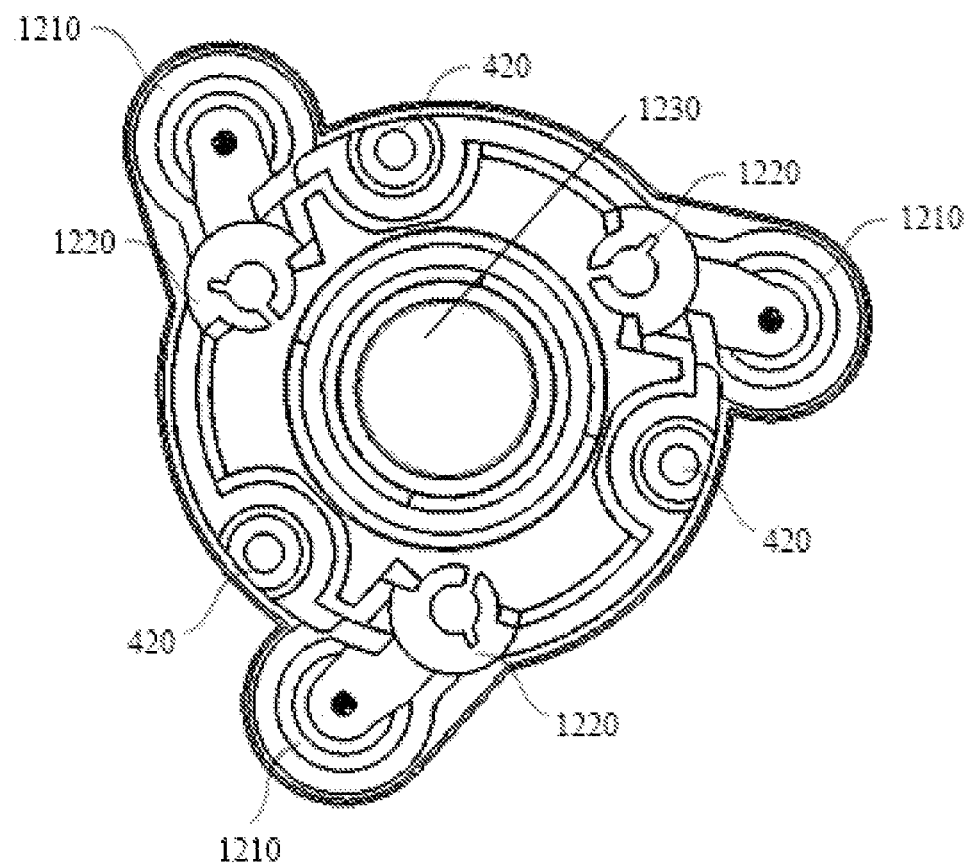
FIG. 13 is a top view diagram of an adaptor base.

Turning now to FIG. 11, shown is a side view diagram of the adaptor base 120. FIG. 12 shows a top oblique view diagram of the top interior of the adaptor base 120. Shown are the three screw holes 420, three perimeter nozzle seats 1210, three valve seats 1220, and a vapor chamber 1230. The screw holes 420 provide the means for screws to be inserted from the underside to attached the adaptor base 120 to the adaptor cap 110. The perimeter nozzle seats 1210 provide terminal support for the perimeter nozzles, and the valve seats 1220 provide the terminal support for the valve flanges enabling the valves to regulate the flow of vapor from the vapor chamber 1230 through to the perimeter nozzles. FIG. 13 shows the top view diagram showing the top interior of the adaptor base 120. Shown are the three screw holes 420, the three perimeter nozzle seats 1210, the three valve seats 1220, and the vapor chamber 1230.

Figure 14:
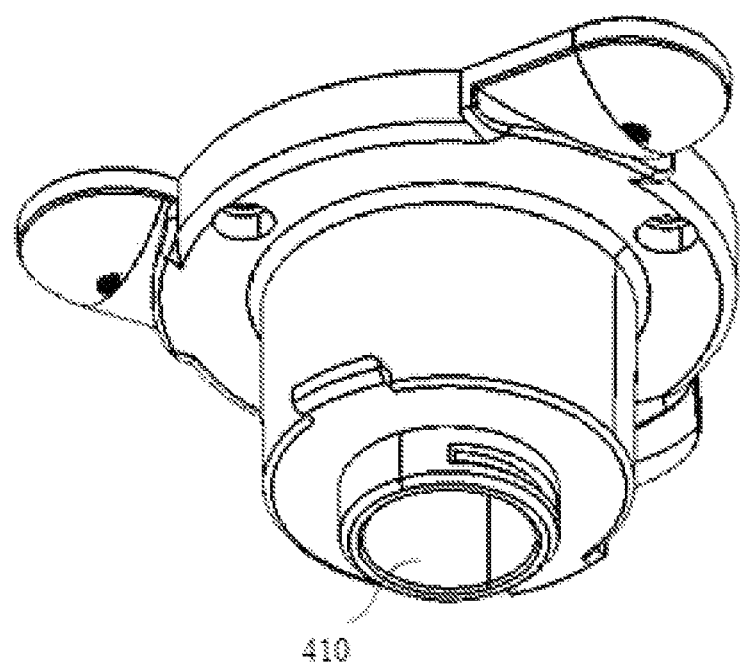
FIG. 14 is a bottom oblique view diagram of an adaptor base.
Figure 15:
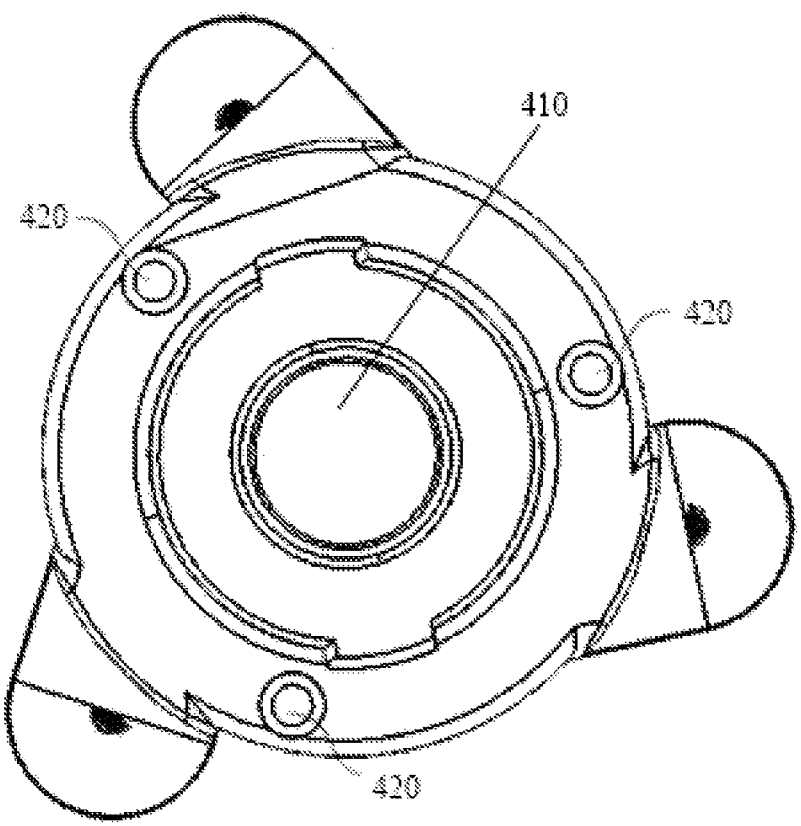
FIG. 15 is a bottom view diagram of an adaptor base.

Turning now to FIG. 14, shown is a bottom oblique view diagram showing the bottom exterior of the adaptor base 120 with the vapor chamber intake vent 410. FIG. 15 shows the bottom view diagram showing the bottom exterior of the adaptor base 120 with the vapor chamber intake vent 410 and the three screw holes 420, each configured to allow a screw to fasten the adaptor base 120 to the adaptor cap 110.

Figure 16:
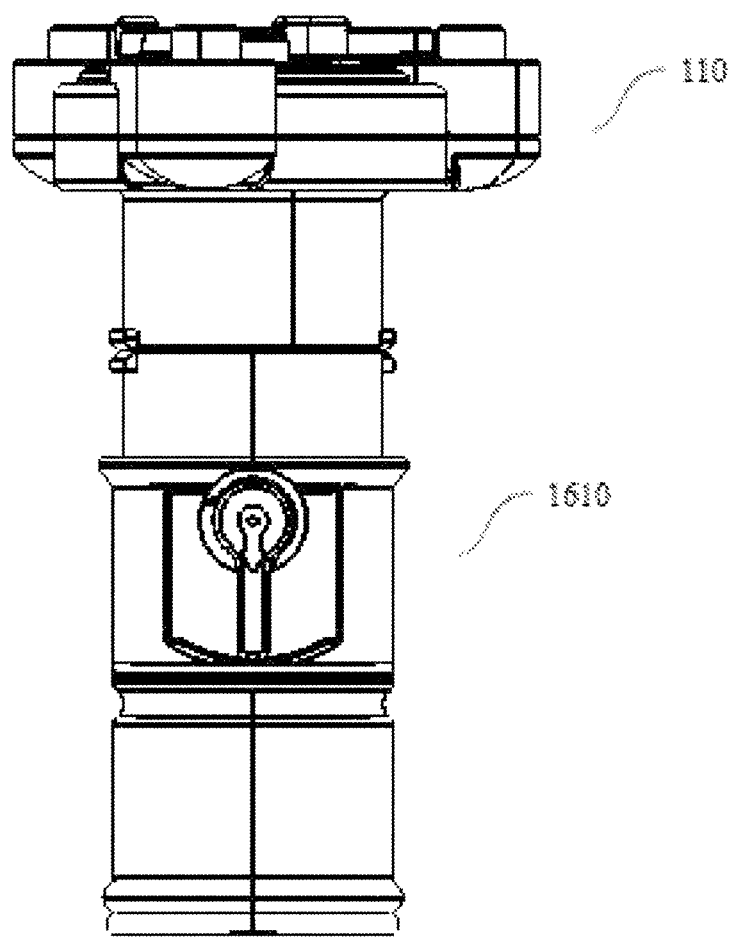
FIG. 16 is a front view diagram of a multi-user inhalation adaptor and balloon adaptor.
Figure 17:
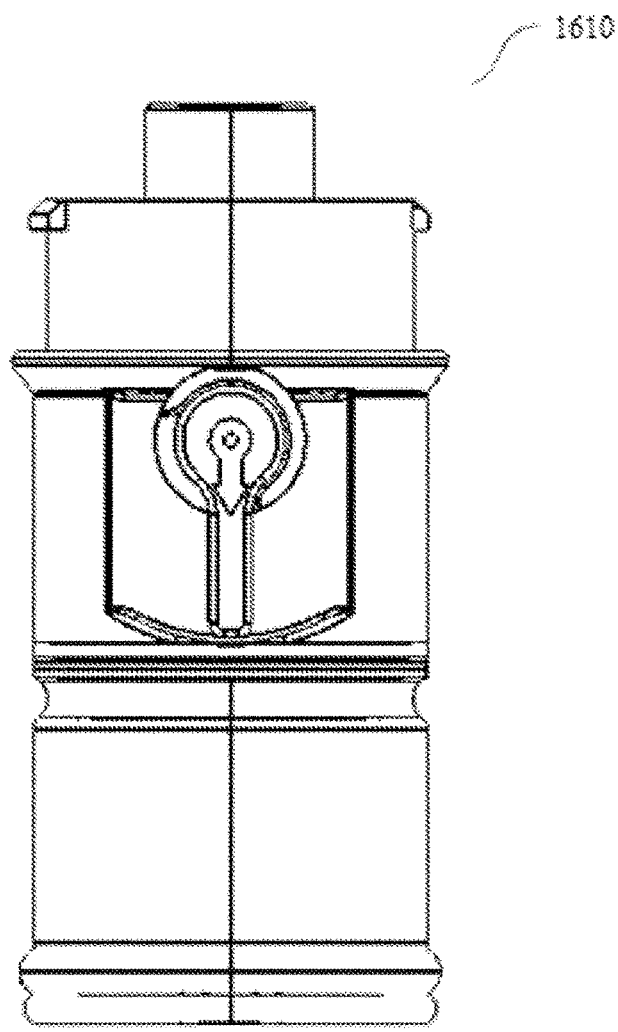
FIG. 17 is a front view diagram of a balloon adaptor.
Figure 18:
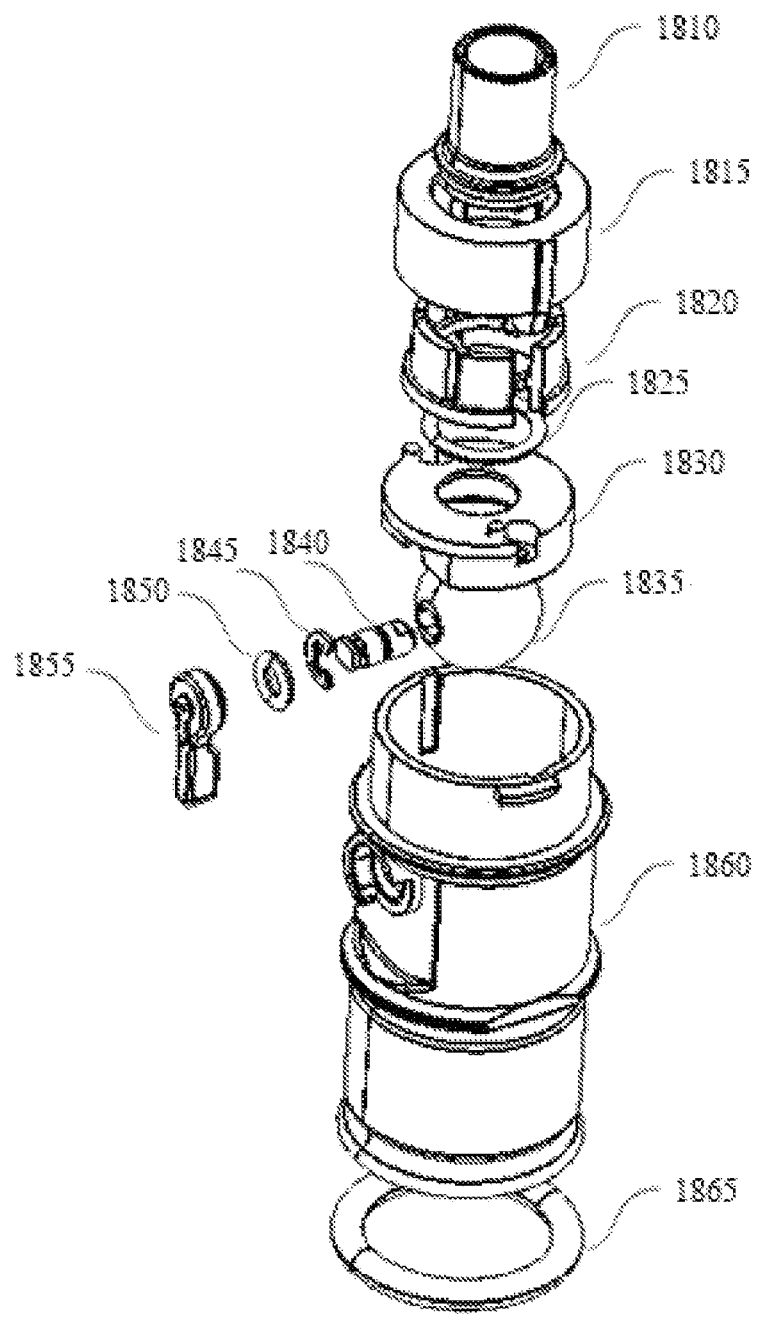
FIG. 18 is an oblique exploded view diagram of a balloon adaptor.

Turning now to FIG. 16, shown is a front view diagram of the multi-user inhalation adaptor 100 and balloon adaptor 1610. The balloon adaptor 1610 is used for obtaining vapor from a storage device such as a balloon. FIG. 17 shows a front view diagram of the balloon adaptor 1610 and FIG. 18 shows an oblique exploded view diagram of a balloon adaptor 1610 showing an interior ball fixture 1810, exterior ball fixture 1815, a mouthpiece lock 1820, a channel O-ring 1825, a ball seal 1830, a valve ball 1835, a valve ball shaft 1840, a valve shaft washer 1845, a valve O-ring 1850, a valve handle 1855, balloon adaptor housing 1860, and a balloon housing O-ring 1865. The interior ball fixture 1810 and exterior ball fixture 1815 provide an interface with the adaptor base so that the balloon adaptor can be attached to the adaptor base. The mouthpiece lock 1820 is situated in the exterior ball fixture 1815, and the channel O-ring 1825 and ball seal 1830 provide support for the balloon adaptor valve comprising the valve ball 1835 fixedly attached to the valve ball shaft 1840 with the valve handle 1855 affixed on the distal end with the valve shaft washer 1845 and valve O-ring 1850 securing valve handle 1855 on the exterior of the balloon adaptor housing 1860. The balloon housing O-ring 1865 is used to secure a balloon to the bottom of the balloon adaptor.

Figure 19:
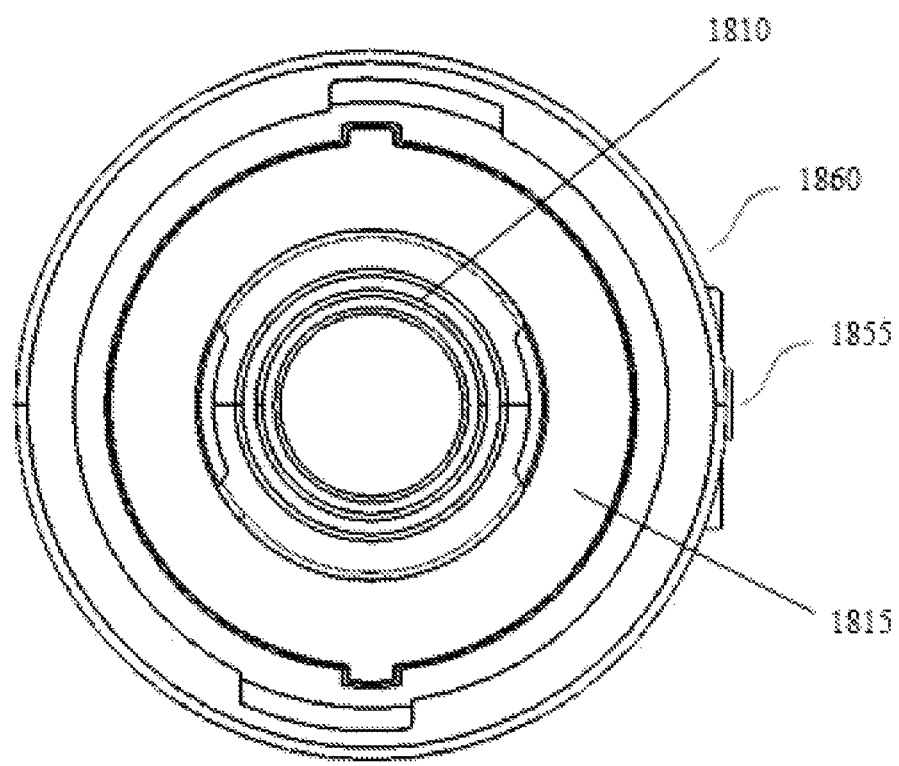
FIG. 19 is a top view diagram of a balloon adaptor.

Turning now to FIG. 19, shown is a top view diagram of the balloon adaptor 1610 showing the interior ball fixture 1810, the exterior ball fixture 1815, the valve handle 1855, and the balloon adaptor housing 1860.

Figure 20:
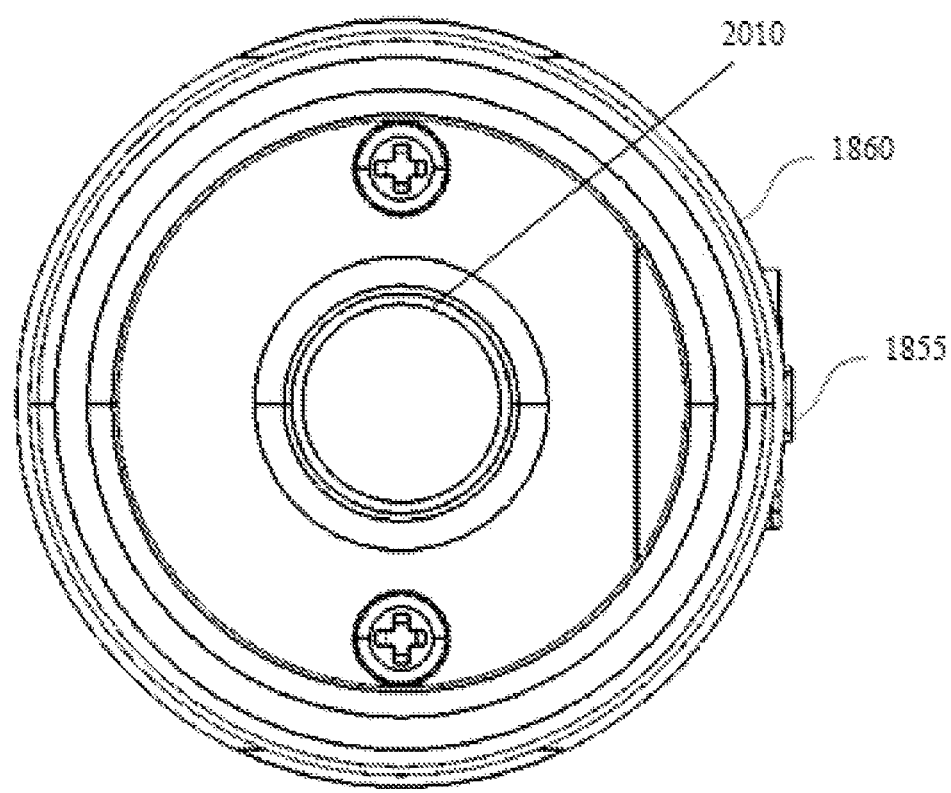
FIG. 20 is a bottom view diagram of a balloon adaptor.

Turning now to FIG. 20, shown is a bottom view diagram of the balloon adaptor 1610 showing the valve handle 1855, the balloon adaptor housing 1860, and the balloon adaptor chamber 2010.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

What is claimed is:

1. A multi-user inhalation adaptor apparatus comprising:
   a. a vapor chamber configured to receive vapor from a vaporizer;
   b. a plurality of perimeter nozzles in communication with said vapor chamber;
   c. a plurality of perimeter nozzle valves, wherein each of said perimeter nozzle valve is associated with a perimeter nozzle and controls communication between said vapor chamber and said perimeter nozzle;
   d. a central nozzle in communication with said vapor chamber;
   e. a plurality of inhalation tubes attached to said central nozzle and said perimeter nozzles;
   wherein a plurality of users can simultaneously inhale said vapor from said vapor chamber through the central nozzle and by opening a plurality of said perimeter nozzle valves.

2. The apparatus of claim 1, wherein said multi-user inhalation adaptor is removably attached to said vaporizer.

3. The apparatus of claim 1 wherein said multi-user inhalation adaptor comprises an adaptor cap, a seal and an adaptor base, wherein said adaptor cap is fastened to said adaptor base said seal is seated between said adaptor cap and said adaptor base.

4. The apparatus of claim 3 wherein said seal provides airflow channels allowing said vapor to flow from said vapor chamber to said perimeter nozzles.

5. The apparatus of claim 3 wherein the bottom of each said perimeter nozzle further comprises a perimeter nozzle intake vent and said adaptor base is configured with a perimeter nozzle seat associated with each said perimeter nozzle intake vent whereby the opening of said perimeter nozzle valve will provide an airflow channel allowing said vapor to flow from said vapor chamber to said perimeter nozzle.

6. A multi-user inhalation adaptor apparatus comprising:
   a. a balloon adaptor;
   b. a vapor chamber configured to receive vapor from said balloon adaptor;
   c. a central nozzle;
   d. a plurality of perimeter nozzles;
   e. a plurality of perimeter nozzle valves, wherein each of said perimeter nozzle valves is associated with a perimeter nozzle;
   f. a plurality of inhalation tubes attached to said central nozzle and said perimeter nozzles;
   wherein a plurality of users can simultaneously inhale said vapor from said vapor chamber through the central nozzle and by opening at least one of said perimeter nozzle valves.

7. The apparatus of claim 6, further comprising an elastic ring means for attaching a balloon to said balloon adaptor.

8. The apparatus of claim 6 wherein said balloon adaptor further comprises a balloon adaptor chamber for receiving vapor from said balloon, and wherein said balloon adaptor chamber is in communication with said vapor chamber.

9. The apparatus of claim 8 wherein said balloon adaptor further comprises a balloon adaptor valve for controlling communication between said balloon adaptor chamber and said vapor chamber.

10. The apparatus of claim 6 wherein said multi-user inhalation adaptor comprises an adaptor cap, a seal, an adaptor base, wherein said adaptor cap is fastened to said adaptor base and said seal is seated between said adaptor cap and said adaptor base, and said adaptor base is attachable to said balloon adaptor.

11. The apparatus of claim 10 wherein said seal provides airflow channels allowing said vapor to flow from said vapor chamber to said perimeter nozzles.

12. The apparatus of claim 10 wherein the bottom of each said perimeter nozzle further comprises a perimeter nozzle intake vent and said adaptor base is configured with a perimeter nozzle seat associated with each said perimeter nozzle intake vent whereby the opening of said perimeter nozzle valve will provide an airflow channel allowing said vapor to flow from said vapor chamber to said perimeter nozzle.

* * * * *